United States Patent [19]
Gentile et al.

[11] Patent Number: 5,086,785
[45] Date of Patent: Feb. 11, 1992

[54] ANGULAR DISPLACEMENT SENSORS

[75] Inventors: Christopher T. Gentile, New York, N.Y.; Michael Wallace, Beaverton; Timothy D. Avalon, Portland, both of Oreg.; Scott Goodman, Hermosa Beach, Calif.; Richard Fuller, Sherman Oaks; Tracy Hall, Cupertino, Calif.

[73] Assignee: Abrams/Gentille Entertainment Inc., New York, N.Y.

[21] Appl. No.: 392,127

[22] Filed: Aug. 10, 1989

[51] Int. Cl.$^5$ .............................................. A61B 5/11
[52] U.S. Cl. ..................................... 128/782; 338/210
[58] Field of Search ..................... 128/774, 782, 721; 338/2, 47, 114, 210-212

[56] References Cited

U.S. PATENT DOCUMENTS 4,444,205  4/1984  Jackson ............................... 128/782
4,745,930  5/1988  Confer ................................. 128/779

Primary Examiner—William E. Kamm
Assistant Examiner—Kevin Pontius

[57] ABSTRACT

A sensor for detecting angular displacement of an object. The sensor comprises a substrate for attachment to the object whose angular displacement is to be sensed and a sensing means attached to the substrate and connectable into an electric circuit. The electric circuit measures the resistance of the sensing means, which changes as a function of the angular displacement. Several embodiments are disclosed, including a conductive elastomer sensor, a conductive ink sensor, a sliding resistor sensor, a force sensitive resistor sensor and a conductive fluid sensor.

3 Claims, 5 Drawing Sheets

FIG. 1a.

STRAIGHT ROD

$\overline{A1\,B1} = \overline{C1\,D1}$

CURVED ROD

$\overline{A2\,B2} > \overline{C2\,D2}$
$\overline{C1\,D1} > \overline{C2\,D2}$
$\overline{A1\,B1} < \overline{A2\,B2}$

STRAIGHT

$\overline{A1\,B1} = \overline{C1\,D1}$

10 — Cord
A1 — E1 — B1
C1 — 12 — D1

FIG. 2b.

CURVED

$\overline{A1\,E1} = \overline{A2\,E2}$
$\overline{B1\,E1} < \overline{B2\,E2}$
$\overline{A2\,B2} > \overline{C2\,D2}$

10, E2
A2, C2 — 12 — B2, D2

V = Voltage
T = Thickness of Conductive Elastomer $\overline{A2\ B2} > \overline{A1\ B1}$
T1 > T2
V1 > V2

V = Voltage
T = Thickness of Conductive Elastomer $\overline{A2\,B2} > \overline{A1\,B1}$
$T1 > T2$
$V1 > V2$ V = Voltage
T = Thickness of Conductive Fluid Tube

ANGULAR DISPLACEMENT SENSORS

BACKGROUND OF THE INVENTION

The present invention relates to sensor technology, and in particular, to sensor technology for detecting angular displacement or bending. Even more particularly, the present invention relates to electrical sensors in which the value of the conductance/resistance and/or conductivity/resistivity of the sensors changes with angular displacement or bending. One application of the present invention would be, for example, to detect the amount of angular displacement or bending of body parts, for example, bending of arms, legs, and fingers of the human body, although other applications may also be found.

Various techniques for determining displacement, deformation or elastic elongation using measurement of resistance, conductance, resistivity or conductivity are known. For example, U.S. Pat. No. 4,748,433 to Jackson et al discloses an electro-conductive elastomer device capable of providing sensory signals representative of elastic elongation.

U.S. Pat. No. 4,444,205 to Jackson shows a device for assessing joint mobility, for example, of human or animal joints.

U.S. Pat. No. 4,715,235 to Fukui et al discloses a deformation sensitive electroconductive knitted or woven fabric.

U.S. Pat. No. 4,639,711 to Edholm et al discloses a deformation sensitive signal transmitter for electric signals which comprises an elastic body consisting of an elastomer matrix containing carbon black as a filling agent.

U.S. Pat. No. 3,820,529 to Gause et al discloses a conductive elastomeric extensometer for measuring surface area changes of the human body.

U.S. Pat. No. 4,273,682 to Kanamori discloses a pressure-sensitive electrically conductive elastomeric composition comprising a substrate composed of an organic flexible material and electrically conductive particles. The composition has such a characteristic that the electric resistivity is reduced under application of pressure.

U.S. Pat. No. 4,252,391 to Sado, U.S. Pat. No. 4,258,100 to Fujitani et al and U.S. Pat. No. 4,152,304 to Tadewald each disclose various pressure-sensitive electrical materials.

U.S. Pat. No. 4,729,809 to Dery et al discloses a conductive adhesive composition.

U.S. Pat. No. 3,332,280 to Fish et al discloses a strain gauge using an electrolyte filled tube for measuring extensions and U.S. Pat. No. 4,461,085 to Dewar et al discloses a goniometer using mercury-in-rubber sensors for use in measuring angular movements of joints of a human or animal body.

U.S. Pat. No. 4,038,867 to Andrews et al discloses a transducer assembly for measuring loads in flexible sheet material and U.S. Pat. No. 3,878,711 to Randolph, Jr. discloses an extensometer comprising an electromechanical deflection sensor mounted in the extensometer to bend or deflect proportionately with the relative movement of the end portions of the device.

U.S. Pat. No. 3,174,125 to Curby discloses a mechanical pressure sensor and U.S. Pat. No. 3,958,455 to Russell discloses a force transducer for a strain gage of the resistance wire type.

U.S. Pat. No. 3,971,250 to Taylor discloses an electret sensing medium having plural sensing units which may be used as a bending stress sensor.

U.S. Pat. No. 4,023,054 to Taylor discloses a strain sensor employing piezoelectric material, U.S. Pat. No. 3,888,117 to Lewis discloses an electromechanical pressure sensor, U.S. Pat. No. 4,429,580 to Testa et al discloses a stress transducer for fabrics and flexible sheet materials, and U.S. Pat. No. 4,258,720 to Flowers discloses a strain gauge plethysmograph.

In addition to the use of conductive material which change resistance or conductivity due to physical movement such as angular displacement, or various electromechanical and transducer arrangements, other types of sensors for determining displacement, bending, flex or other physical parameters such as deformation and stress are known.

For example, U.S. Pat. No. 4,542,291 to Zimmerman discloses an optical flex sensor which may be used to determine the amount of bending, for example, of a finger of the human hand.

U.S. Pat. No. 4,414,537 to Grimes discloses a digital data entry glove interface device which utilizes sensors disposed on a glove positioned with respect to the hand for detecting the flex of finger joints. The flex sensors, as shown in FIGS. 4 and 5 of that reference are optical in nature, relying upon the constriction of a tube in order to determine the amount of flex. Furthermore, the flex sensor of that reference is primarily a digital device, since it is incapable of determining further flexure beyond a given point when the optical tube is completely closed off by the flexure.

The flex sensor of the Zimmerman patent, U.S. Pat. No. 4,542,291, utilizes a flexible tube having an interior wall covered with a reflective material and uses a combination of reflected and direct light received at the receiver to determine the amount of flex. However, the flex sensor of that reference also suffers from an inability to determine accurately the amount of flex beyond a given point.

U.S. Pat. No. 4,269,506 to Johnson et al discloses an apparatus for measuring the influence of physical parameters such as temperature, pressure and force on the length of a path. This system uses an elastically stretchable optical fiber to determine length changes based upon travel times through the optical fiber.

U.S. Pat. No. 4,420,251 to James et al discloses an optical deformation sensor which is responsive to, for example, fatigue, vibration, flex, torsion, bending or slippage.

U.S. Pat. No. 4,123,158 to Reytblatt discloses a photoelastic strain gauge

U.S. Pat. No. 4,191,470 to Butter discloses a laser-fiber optic interferometric strain gauge U.S. Pat. No. 3,517,999 to Weaver discloses an optical strain gauge U.S. Pat. No. 3,229,511 to Rossire discloses an optical stress sensor for an aircraft.

None of the above sensors have provided a simple, reliable means for accurately measuring, over a wide range of values, angular displacement or bending, for example, of human joints such as finger joints.

SUMMARY OF THE INVENTION

Accordingly, it is an object of the present invention to provide a sensor which is capable of accurately providing a signal related to the amount of angular displacement of a body to which it is attached.

It is a further object of the present invention to provide an angular displacement sensor which measures change in electrical conductance, conductivity, resistance or resistivity in order to determine the amount of bending or angular displacement of an item to which the sensor is attached.

It is furthermore an object of the present invention to provide such an angular displacement sensor which can be employed for measuring the angular displacement of human being or animal body parts, for example, the fingers of the hand, movement of arms and legs and other joints.

In particular, the angular displacement sensors of the present invention may be employed in conjunction with a glove for the hand or a body suit for a person in order to provide inputs to a computer relating to such movement. For example, the angular displacement sensors of the present invention may be disposed on a glove worn by a user such that movement of the fingers of the user can be supplied as inputs to a computer to control robotics, video games, the movement of graphics or other displayed material on a display terminal and a host of other applications which will be apparent from the description which follows.

The above and other objects are achieved according to one embodiment of the present invention by a sensor for detecting angular displacement of an object comprising a substrate for attachment to the object whose angular displacement is to be sensed, sensing means attached to the substrate and connectable into an electric circuit, the sensing means comprising a material having an electrical resistance which changes as a function of the angular displacement, the material comprising an electrically conductive ink deposited on the substrate.

According to another embodiment of the present invention, the above objects are achieved by a sensor for detecting angular displacement of an object comprising a substrate for attachment to the object whose angular displacement is to be sensed, sensing means attached to the substrate and connectable into an electric circuit, the sensing means comprising a material having an electrical resistance which changes as a function of the angular displacement, the material comprising an electrically conductive elastomer bonded to the substrate along the length of the substrate, the substrate having a flex characteristic different from that of the elastomer to minimize hysteresis in the elastomer so as to return the elastomer to its straightened position after an angular displacement.

According to yet another embodiment of the present invention, the above objects are achieved by a sensor for detecting angular displacement of an object comprising a substrate for attachment to the object whose angular displacement is to be sensed, sensing means attached to the substrate and connectable into an electric circuit, the sensing means comprising a material having an electrical resistance which changes as a function of the angular displacement, the material comprising an electrically conductive fluid disposed in a hollow longitudinally extending member, the hollow member changing in cross sectional area during angular displacement.

According to yet another embodiment of the invention, the above objects are achieved by a sensor for detecting angular displacement of an object comprising a substrate for attachment to the object whose angular displacement is to be sensed, sensing means attached to the substrate and connectable into an electric circuit, the sensing means comprising a longitudinally extending substantially nonstretchable member fixed at one end to the substrate and having a free end, a variable resistance means being attached to the substrate adjacent the free end and having a movable member and a fixed resistor, the movable member being coupled to the free end and movably in electrical contact with the fixed resistor for providing a resistance value with respect to an end of the fixed resistor which varies as a function of the location of the movable member.

According to yet still another embodiment of the invention, the above objects are achieved by a sensor for detecting angular displacement of an object comprising a substrate for attachment to the object whose angular displacement is to be sensed, sensing means attached to the substrate and connectable into an electric circuit, the sensing means comprising a longitudinally extending substantially nonstretchable member fixed at one end to the substrate and having a second end, a force sensitive resistor being disposed adjacent the substrate, the second end being in contact with the resistor so as to apply a force to the resistor, the force applied changing in relation to the amount of angular displacement of the substrate.

Other objects, features and advantages of the present invention will be apparent from the detailed description which follows.

BRIEF DESCRIPTION OF THE DRAWINGS

The invention will be described in greater detail in the following detailed description with reference to the drawings, in which:

FIGS. 1a and 1b explain what is meant by angular displacement;

FIGS. 2a and 2b show how angular displacement can be translated into a change in position;

DETAILED DESCRIPTION

Figure 3A:
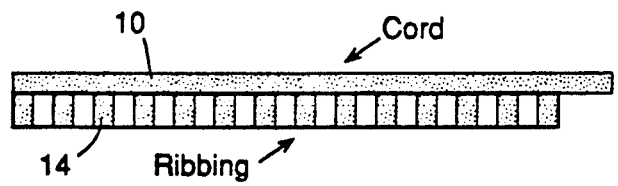
FIGS. 3a and 3b show how performance of an angular displacement sensor can be enhanced by disposing the sensor material across a ribbed substrate.

Angular displacement refers to the change in distance across a corner or bend as the bend angle or amount of bend changes. As the corner's angle changes, the angular displacement changes. A sensor for measuring angular displacement will measure the change in distance across the corner as the corner's angle changes. Put another way, an angular displacement sensor measures the change in distance which occurs on the outside of a bent object. A typical application for this type of sensor would be determining whether a door was open, closed or somewhere in between open and closed. Other applications include the measurement of the amount of bending of a human joint, for example, the finger of a hand.

According to the invention, five different technologies are provided for measuring changes in angular displacement by measuring changes in electrical resistance, resistivity, conductance or conductivity. These technologies include conductive elastomer, conductive ink, conductive fluid, slide resistor and force resistor sensors. These technologies determine angular displacement via stretch (conductive elastomer, ink and fluid), position (slide resistor) or force applied (force resistor).

With reference now to FIG. 1 of the drawings, angular displacement is the change in distance which occurs on the outside of a bent object. In FIG. 1a, a flexible vinyl rod is shown in a straight position. As this vinyl rod is bent, as shown in FIG. 1b, the rod's inside relaxes while the outside stretches. This causes the inside length to decrease from its original value while the outside length increases. The inequalities in FIG. 1b show how angular displacement may be measured, i.e., the displacement may be measured by detecting the amount of change of the distance A2B2 versus A1B1 or the change in distance C2D2 versus C1D1. Furthermore, the angular displacement may also be measured by comparing A2B2 to C2D2. The conductive elastomer, ink and fluid sensors according to the invention rely on this stretching effect in order to determine angular displacement, although instead of actually measuring distances, the change in electrical resistance/conductance and/or resistivity/conductivity with bending is sensed.

The sensors according to the invention for measuring angular displacement based on a change in position or force are derived on one common application called the angular displacement translator, see FIG. 2, which is useful for explaining how the sensors work. A flexible cord 10 is mounted across the outside-bend area of the sensor. One end of the cord is attached permanently to the substrate 12, while the other end and the interface between the cord and the substrate 12 are left unbonded. As a bend occurs, as shown in FIG. 2b, the outside distance increases and the cord slides over the outside surface toward the permanently attached end. This application translates angular displacement into a change in relative position which can also be interpreted as a change in applied force. As shown in FIG. 2, as the distance A2E2 equals A1E1 remains constant, the angular displacement may be measured by comparing distance B2E2 with distance B1E1.

Figure 3B:
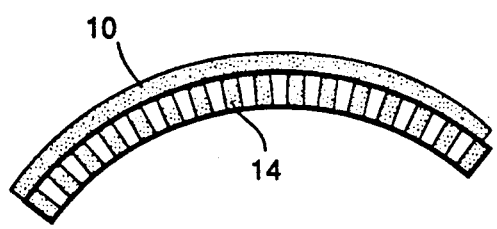

FIG. 3 shows how the performance of the angular displacement translator of FIG. 2 can be enhanced by mounting the cord 10 across a flexible material 14 with ribbing running perpendicular to the cord. As a bend occurs, the ribbing will spread at the point of bend, thus amplifying the outside bend distance. The greater the height of the ribbing the greater the amplification. This is shown by the fact that the outside length of the ribbed material has increased to the point that the cord, which formerly was longer than the length of the ribbed material, now has a length approximately equal to the curved outside length of the ribbed material. If the cord 10 instead was attached to the ribbing along its length, it would be stretched more than a corresponding cord attached to a smooth unribbed substrate. This angular displacement "amplifier" can be used with the conductive elastomer, ink and fluid and force resistor sensors discussed herein to amplify the angular displacement signal provided by the sensor.

The first technology to be discussed for measuring angular displacement uses conductive elastomer. This is a rubber-like material with elastic properties which has been manufactured with compounds which enable it to conduct electricity, typically carbon impregnated flexible rubber, silicone, plastic, etc. Conductive elastomers are commonly used in electronic keypads and in antistatic products and typically comprise a mixture of silicone rubber and carbon.

One of the factors affecting the conductivity/resistivity and, accordingly, conductance/resistance of the elastomer material are its dimensions, specifically, its length and cross sectional area. Altering the length of the material with a constant cross sectional area will changes its conductivity, such that the shorter the material, the greater its conductivity.

Likewise, if the cross sectional area is altered while its length remains constant, a change in conductivity will take place such that the greater the cross sectional area of the material the greater its conductivity.

Figure 4A:
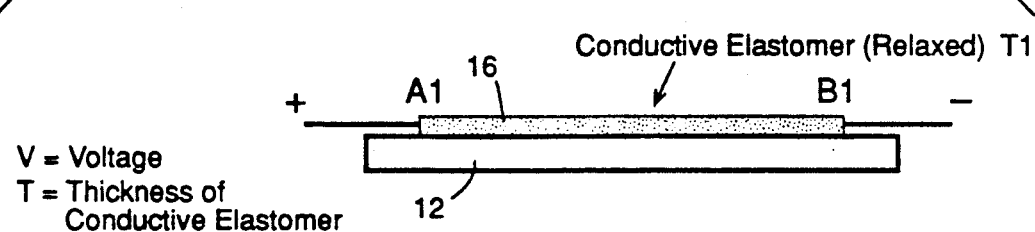
FIGS. 4a and 4b show a conductive elastomer angular displacement sensor.
Figure 4B:
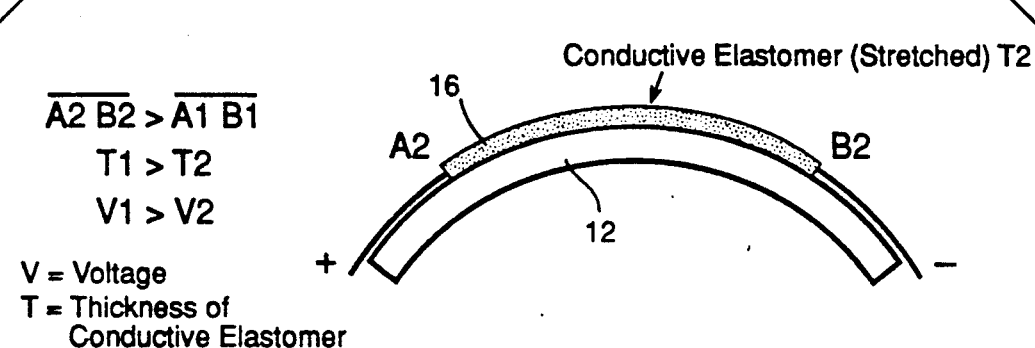

When a conductive elastomer is stretched, its length increases and its cross sectional area decreases. This will dramatically alter its conductive characteristics. As a conductive elastomer strip is stretched, its resistivity will rise. This property makes conductive elastomers very practical for measuring lengthwise positional changes, i.e., stretch. As shown in FIG. 4, the conductive elastomer sensor comprises a conductive elastomer 16 mounted on a substrate 12. Both ends of the conductive elastomer material 16 are mounted permanently and the conductive elastomer is preferably cemented along its interface with the substrate to the substrate. As a bend as shown takes place, there is no slippage at either end and stretching of the conductive elastomer material occurs. An electrical voltage is applied to the sensor and the change in current, which will be proportional to the change in resistance, may be measured to determine the amount of bending. Alternatively, the sensor can be mounted in a voltage divider arrangement, and a change in voltage across the sensor with bending can be measured, the voltage across the sensor varying according to the degree of stretch induced by the amount of bending.

Figure 5A:
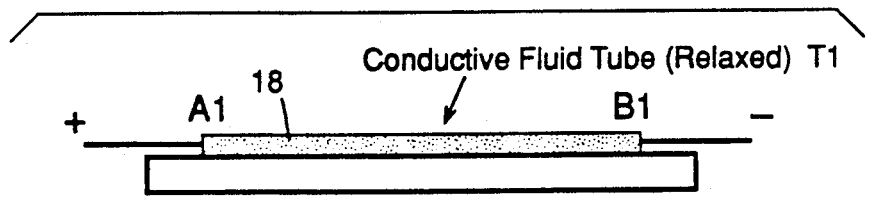
FIGS. 5a, 5b and 5c show a conductive fluid angular displacement sensor.
Figure 5B:
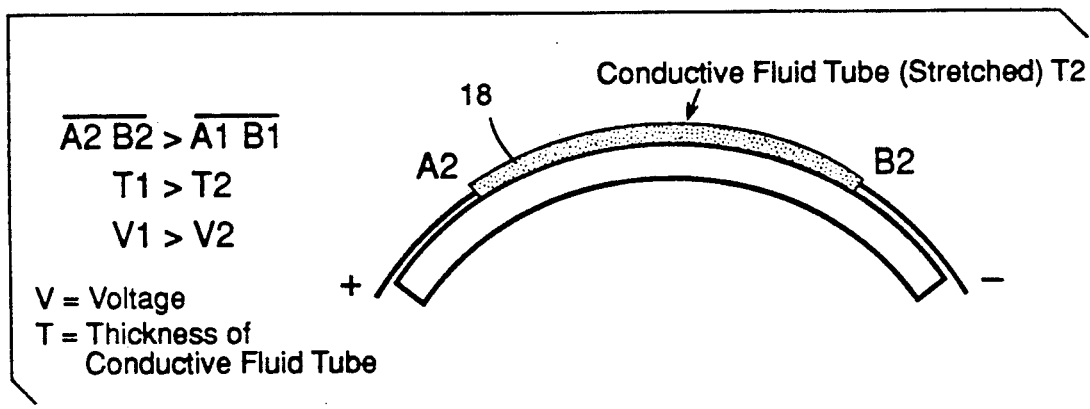
Figure 5C:
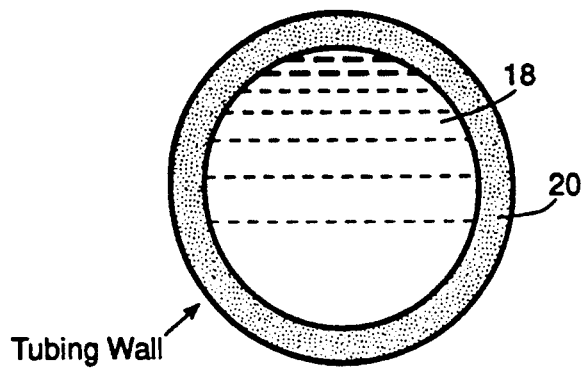

FIG. 5 shows another angular displacement sensor comprising a conductive fluid sensor. The conductive fluid 18 is a material with the property of a fluid which conducts electricity like electrolytic solutions or conductive oils. The conductive fluid is contained inside an elastic tube 20 as shown in FIG. 5c. As the elastic tubing is stretched, the length of the tubing and thus the conductive fluid increases while its cross sectional area decreases, causing a rise in its resistance. See FIG. 5b. The conductive fluid sensor operates in much the same manner as the conductive elastomer sensor of FIG. 4, i.e., it measures the degree of stretch induced by an angular bend.

Figure 6A:
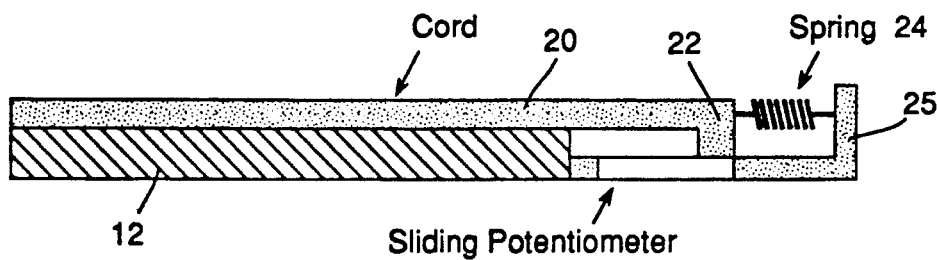
FIGS. 6a and 6b show a slide resistor angular displacement sensor.
Figure 6B:
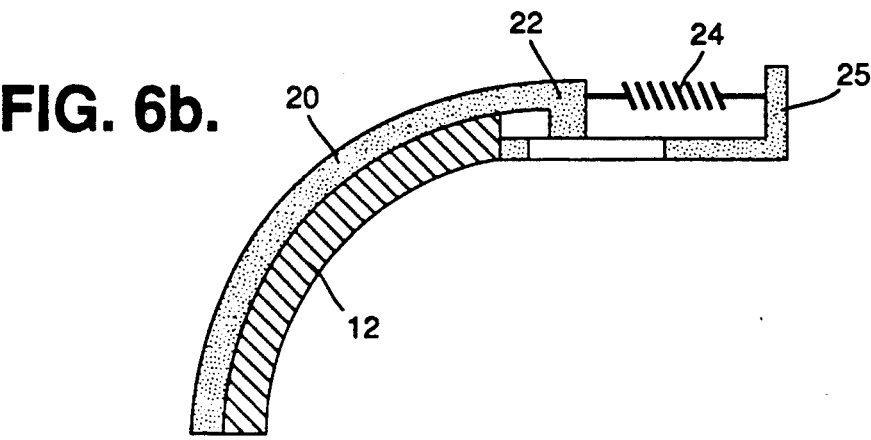

FIG. 6 shows a sliding resistor sensor which is a sliding potentiometer to measure angular displacement. A cord 20 is mounted across the sensor area and fixed only at one end to the substrate 12. The interface between the cord and the substrate is also left free. The free end is attached to movable member 22 of the sliding potentiometer. As the degree of bend increases, the cord will slide relatively towards the fixed end, moving the sliding potentiometer against the action of a spring or other elastic material 24. The spring or other elastic material is coupled between the movable member and a retainer 25. As the bend decreases and the cord is relaxed, the spring or other elastic material keeps the slack out of the sensor.

Figure 7A:
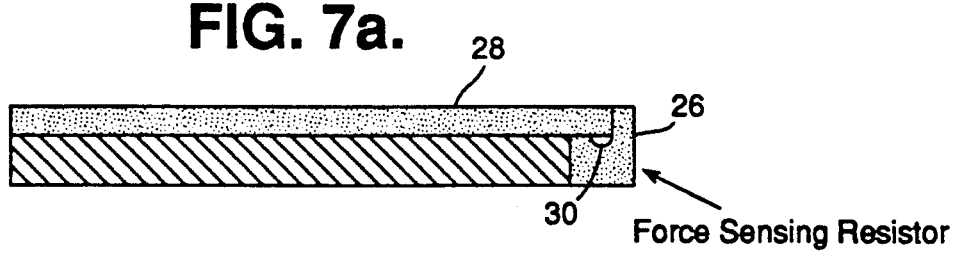
FIGS. 7a and 7b show a force sensing resistor angular displacement sensor.
Figure 7B:
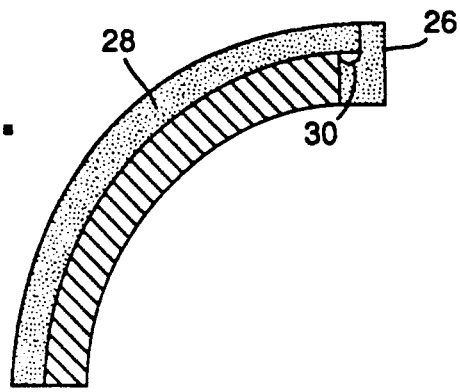

FIG. 7 shows a force resistor sensor type of bend sensor. The force resistor sensor converts a translated angular displacement into a proportional force applied against a force sensing resistor 26. An elastic rubber-like material 28 is used as an angular displacement translator. A protrusion 30 located at one end of the translator is disposed directly above the force sensing resistor 26. As a bend occurs, the protrusion 30 applies more and more pressure against the force sensing resistor, which changes its resistance in a relationship to the amount of force applied. The force sensitive resistor may comprise, for example, a pressure sensitive material as shown in U.S. Pat. Nos. 4,273,682 to Kanamori or 4,250,391 to Sado. Force sensitive resistors may comprise a conductive ink deposited on a substrate.

Figure 8:
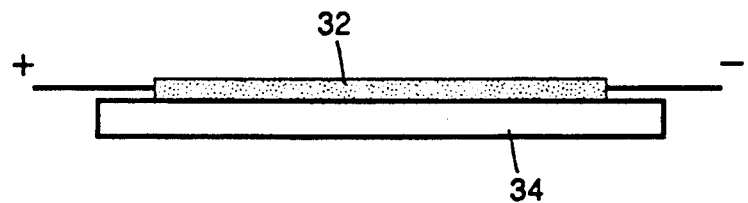
FIG. 8 shows a conductive ink angular displacement sensor.

FIG. 8 shows a conductive ink sensor which utilizes a conductive ink 32 printed or deposited onto a substrate 34 such as Mylar ® or Captan ®. Conductive inks typically comprise carbon particles in a binder. When the substrate is bent such that the printed ink is on the outside of the bend, two physical reactions within the ink cause a change in its electrical resistance. In the first physical reaction, the ink stretches causing the distances between the conductive carbon particles to increase. This causes a very steady, predictable increase in electrical resistivity. This physical reaction also occurs when the conductive ink is on the inside of the bend, with the distances between particles decreasing, thus decreasing resistivity.

By a second physical reaction, micro cracks form transversely to the longitudinal extent of the sensor when the conductive ink is on the outside of the bend. As the bend increases, the width of these cracks increases causing a more dramatic increase in electrical resistance.

Two ink formulas may be mixed to create the conductive ink utilized in the bend sensor according to the invention, depending on the particular characteristics desired. A more durable stretchable ink formula embodies the characteristics of the first physical reaction and a second ink formula is more brittle and embodies the characteristics of the second physical reaction. These two inks may be mixed to customize the performance of the bend sensor. A suitable ink comprising a combination of both ink types can be obtained from Amtech International, Lot 92349. These inks are typically used in making potentiometers. When a greater percentage of the second ink is used, the rise of resistance versus bend is much sharper and higher. It has been found that for use where a high amount of resolution is desired, a higher percentage of the second ink should be used. For durability and average resolution, e.g., subdivision of the resistance range into approximately 4 levels, a higher percentage of the first ink should be used. In particular, for use in a bend sensor to be affixed to a glove for determining hand positions for inputting data into a video game controller with four levels of resolution, the conductive ink identified above Amtech Lot 92349 comprising a selected percentage of the first ink and the remainder the second ink is preferable. A sensor using this ink is available from Amtech International as part No. AM4000 Rev. G, made in accordance with applicants' specifications.

Unlike conductive elastomers, a conductive ink bend sensor does not exhibit a memory when bent toward the straight position. Thus, the conductive ink sensor does not exhibit hysteresis as the conductive elastomer sensors do. Therefore, the resistance returns to the same resistance value in its straight unbent position each time.

In contrast, conductive elastomers tend to have a memory such that the resistance does not return to its initial value when straightened. In order to decrease this tendency, it is preferable to mount a conductive elastomer, as shown in FIG. 4, on a substrate which has a different physical flexing characteristic than the elastomer such that it returns to its straight position easily, in order to reduce the amount of hysteresis in the elastomer by straightening the elastomer as much as possible. A suitable material for the substrate might be a Mylar ® film, for example, which readily springs back to its unflexed position after a flexure.

Figure 8A:
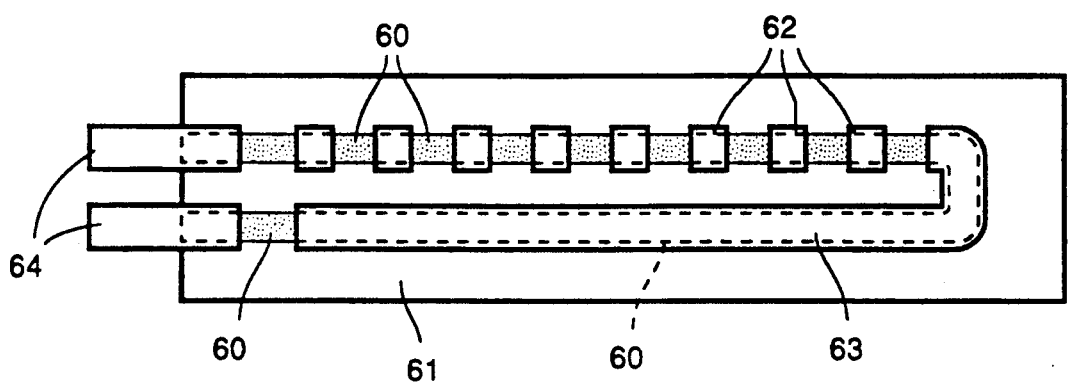
FIG. 8a shows a top view of an alternative embodiment of a conductive ink angular displacement sensor.

FIG. 8a shows an alternative embodiment of a conductive ink angular displacement sensor. The sensor includes a conductive ink 60 deposited in a U-shape on a flexible substrate 61 such as mylar or Captan. Because the resistance of such inks (for the length of an actual sensor of approximately 4 inches) is typically high, in the megohm range, the sensor resistance range may be translated into a lower range essentially by depositing a highly conductive material, such as a metallic material, over the conductive ink in selected areas 62 in effect creating a series of individual conductive ink sensors whose combined resistance is less than a sensor not containing the metallic deposits. Furthermore, the sensor can be thus tailored to have any give needed resistance range by selectively covering larger portions of the ink 60, as needed. Metal end terminal connections are indicated at 64 and reference numeral 63 denotes, for example, a long plated section of the metallic conductive material covering an entire leg of the U-shaped conductive ink deposit and coupling one of the terminals 64 with the end of the useful portion of the conductive ink 60. Thus, in effect, only those portions of the conductive ink 60 not covered by the metallic material will be effective in determining the amount of flex.

Figure 9A:
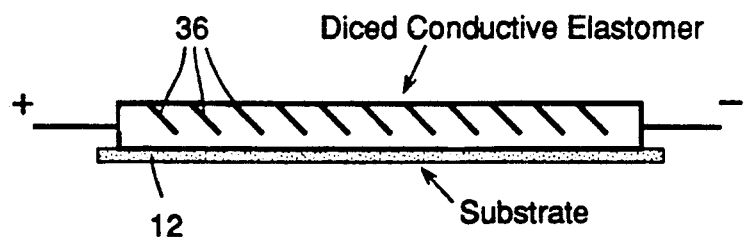
FIGS. 9a and 9b show a diced conductive elastomer angular displacement sensor.
Figure 9B:
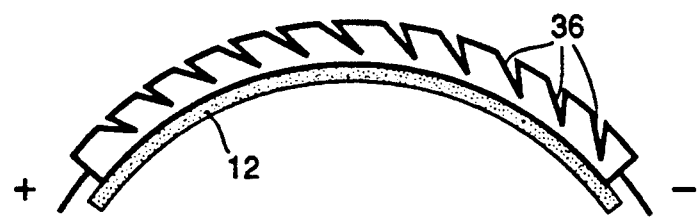

FIG. 9 shows a diced conductive elastomer sensor which incorporates diagonal slices 36 as shown in FIG. 8a into the construction of a conductive elastomer sensor. The slices widen as the degree of bend increases, causing an increase in electrical resistance. As the sensor is straightened, the slices close and the electrical resistance decreases. This design helps to minimize the memory effect or hysteresis of the conductive elastomer.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. A sensor for detecting angular displacement of an object comprising:
   a substrate for attachment to the object whose angular displacement is to be sensed;
   sensing means attached to the substrate and connectable into an electric circuit, the sensing means comprising a material having an electrical resistance which changes as a function of the angular displacement, said material comprising an electrically conductive ink deposited on said substrate, said conductive ink comprising carbon particles in a binder and further comprising a solution of a first stretchable ink and a second brittle ink.

2. The sensor recited in claim 1, wherein said first and second inks are mixed in order to customize the sensor to an application, said first ink providing durability and said second ink providing a higher resistance range.

3. A sensor for detecting angular displacement of an object comprising:

a substrate for attachment to the object whose angular displacement is to be sensed;

sensing means attached to the substrate and connectable into an electric circuit, the sensing means comprising a material having an electrical resistance which changes as a function of the angular displacement, said material comprising an electrically conductive ink deposited on said substrate, and further comprising a highly conductive material deposited on the conductive ink in at least one selected area.

* * * * *